United States Patent [19]

Avar et al.

[11] Patent Number: 5,821,288
[45] Date of Patent: Oct. 13, 1998

[54] ORGANIC COMPOUNDS

[75] Inventors: Lajos Avar, Bruggmatt, Switzerland; Roland Joseph Valin, Cranbury, N.J.

[73] Assignee: Clariant Finance (BVI) Limited, Tortola, Virgin Islands (Br.)

[21] Appl. No.: 659,843

[22] Filed: Jun. 7, 1996

[30] Foreign Application Priority Data

Jun. 7, 1995 [GB] United Kingdom ............... 9511486

[51] Int. Cl.$^6$ .................................................. C08K 5/3445
[52] U.S. Cl. ............................... 524/91; 524/99; 524/102
[58] Field of Search ............................ 524/99, 102, 222, 524/91

[56] References Cited

U.S. PATENT DOCUMENTS

| | | | |
|---|---|---|---|
| 3,808,273 | 4/1974 | Burdet et al. | 524/102 |
| 4,408,051 | 10/1983 | Hinsken et al. | 524/102 |
| 4,780,494 | 10/1988 | Hess | 524/99 |
| 4,797,436 | 1/1989 | Ertl | 524/97 |
| 4,920,169 | 4/1990 | Avar | 524/102 |
| 4,929,652 | 5/1990 | Gugumus | 524/100 |
| 5,106,891 | 4/1992 | Valet | 524/102 |

*Primary Examiner*—Paul R. Michl
*Attorney, Agent, or Firm*—Miles B. Dearth; Gabriel Lopez

[57] ABSTRACT

A coating composition comprising
  a) a film-forming material
  b) a stabilizing effective amount of a light stabilizing composition which comprises a blend of at least one diphenyloxamine of the formula

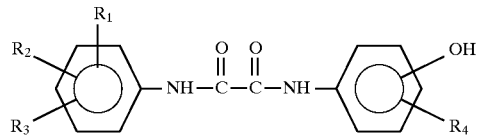

where
  $R_1$ is hydrogen, alkyl, alkoxy or halogen;
  $R_2$ is hydrogen, alkyl, alkoxy, halogen, phenyl or phenoxy; and
  $R_3$ and $R_4$ are hydrogen, alkyl or alkoxy and at least one selected tetraalkylpiperidine.

In a preferred embodiment, a benzotriazole is also present in the light stabilizing composition.

The coating compositions are especially useful for the automotive market.

The invention further relates to a method for enhancing the light stability of coatings comprising adding to the solids content of the coating composition a stabilizing quantity of the above-mentioned light stabilizing composition. The invention also relates to the corresponding stabilized coating film.

5 Claims, No Drawings

ORGANIC COMPOUNDS

This invention relates to light-stabilizing compositions and to polymeric compositions containing such light-stabilizing composition.

Many polymeric compositions are exposed to high levels of light during their service life. The coating compositions which are applied to motor vehicles are examples of such polymeric compositions as the vehicles to which they are applied are frequently left out in the sun for prolonged periods. Light, and in particular ultra-violet (UV) light, has deleterious effects on coating films; the best known of these effects are the fading of the colour and the degradation of the film-forming polymer of the coating composition. To counteract these effects, it is usual to include in such polymeric compositions additives whose function is to counteract the effects of UV radiation and thus prolong the service life of the polymeric composition. Various classes of compounds have been disclosed in the art. One example of a group of compounds is the benzotriazoles which have been used as UV absorbers for some time. Another class is the diphenyloxamides typical examples of which are described in U.S. Pat. No. 3,808,273. A more recent class of materials are the hindered amine light stabilizers (HALS) one class of which is the tetraalkylpiperidines.

It has now been found that a particular combination of such stabilizers can give especially efficacious results, especially when used in coating compositions, and particularly those for use on motor vehicles. There is therefore provided, according to the present invention, a light stabilizing composition which comprises at least one diphenyloxamide and at least one tetraalkylpiperidine, the diphenyloxamide being selected from compounds of formula I

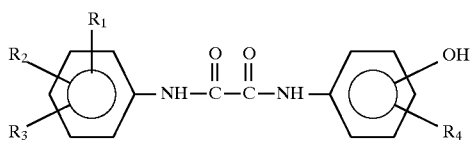

(I)

wherein $R_1$ is selected from hydrogen $C_{1-20}$alkyl, $C_{1-20}$alkoxy and halogen;

$R_2$ is selected from hydrogen, $C_{1-20}$alkyl, $C_{1-20}$alkoxy, halogen, phenyl and phenoxy; and $R_3$ and $R_4$ are selected from hydrogen, $C_{1-20}$alkyl and $C_{1-20}$alkoxy; and the tetraalkylpiperidine is selected from compounds of formulae II–IX

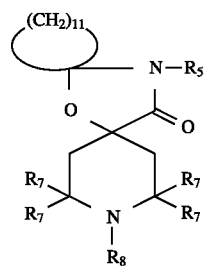

(II)

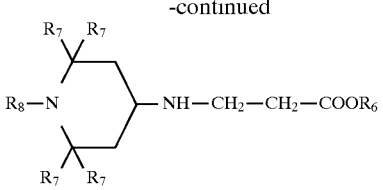

(III)

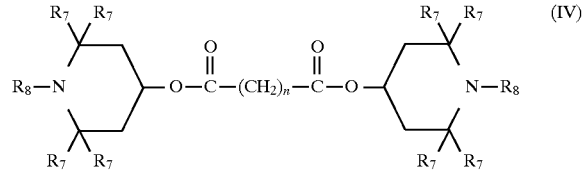

(IV)

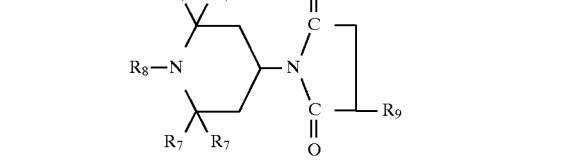

(V)

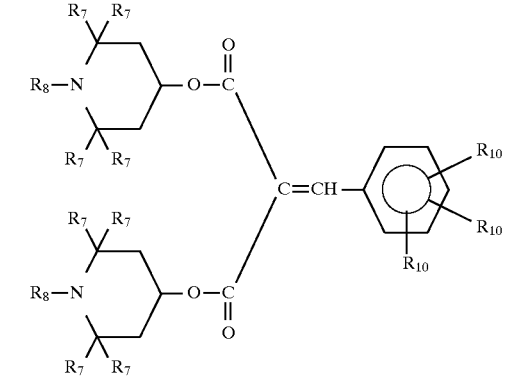

(VI)

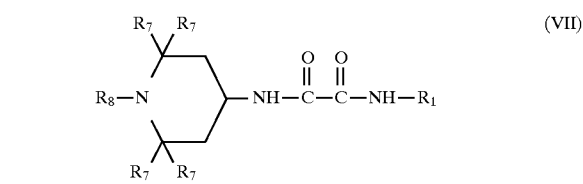

(VII)

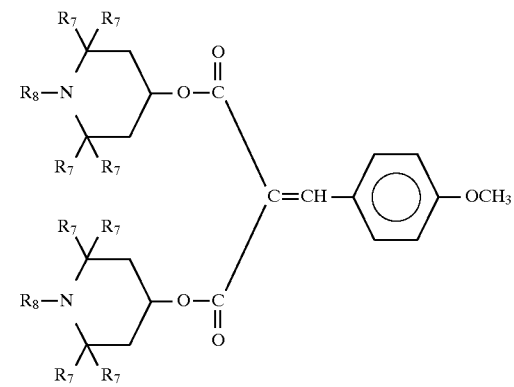

(VIII)

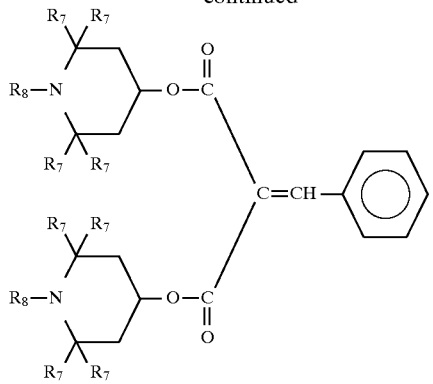

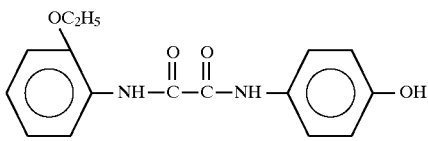

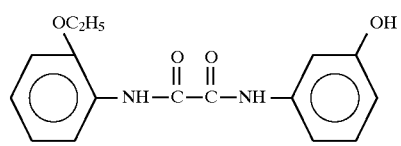

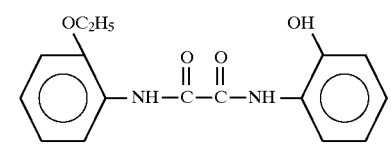

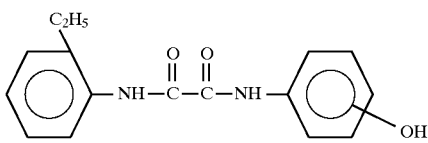

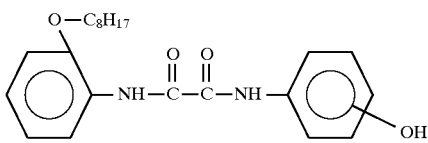

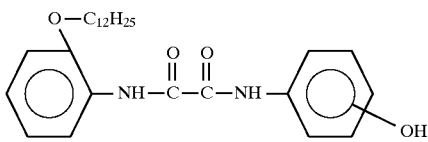

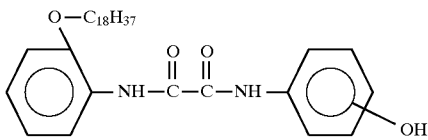

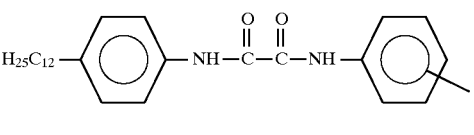

wherein $R_5$ is selected from hydrogen and a group of the formula —$(CH_2)_n$—$COOR_6$ wherein $R^6$ is $C_{1-18}$alkyl;

each $R_7$ is selected from $C_{1-6}$alkyl, preferably methyl, or two groups $R_7$ attached to the same piperidine carbon atom form together with that carbon atom a saturated isocyclic ring of six carbon atoms maximum;

$R_8$ is selected from hydrogen, $C_{1-18}$alkyl, $C_{1-18}$alkylcarbonyl, $C_{1-18}$alkoxy, —$COR_{13}$ where $R_{13}$ is —$C(R_{14})$=$CH_2$; $C_{1-6}$ alkyl; phenyl; —$NR_{15}R_{16}$; —CO—$C_6H_5$; —$CH_2C_6H_5$; —$COOC_{1-12}$alkyl or —COOH; $R_{15}$ is hydrogen, $C_{1-12}$alkyl, $C_{5-6}$cycloalkyl, phenyl, phenyl $C_{1-4}$alkyl or $C_{1-12}$ alkylphenyl and $R_{16}$ is hydrogen or $_{1-12}$alkyl; and $R_{14}$ is hydrogen or $C_{1-6}$alkyl unsubstituted or monosubstituted by OH;

$R_9$ is $C_{1-18}$alkyl;

$R_{10}$ is independently selected from hydrogen, $C_{1-12}$alkyl, $C_{1-12}$alkoxy, —OH or

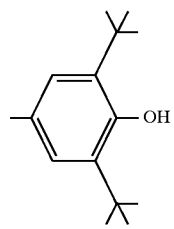

$R_{11}$ is selected from $C_{1-18}$alkoxy and Ph $OCH_2COOR_6$ where Ph is phenyl;

n is a number from 1 to 18; and m is a number from 1 to 4;

the diphenyloxamide and the tetraalkylpiperidine being present in the composition in the proportion of from 1:19 to 19:1.

In this specification, any group capable of being linear or branched is linear or branched unless the contrary is specifically indicated, and where a symbol appears more than once in a formula, its significances are independent of one another.

In a preferred embodiment of the invention, $R_2$ and $R_3$ are hydrogen. In another preferred embodiment, $R_4$ is hydrogen. In a more preferred embodiment, $R_2$, $R_3$ and $R_4$ are hydrogen. In a still more preferred embodiment, $R_1$ is selected from $C_{1-20}$alkyl and $C_{1-20}$alkoxy. Still more preferred is the case wherein this $R_1$ is in the 2- or 4-position. Specific examples of most preferred diphenyloxamides have the formulae Ia–Ih The compound of formula Ia is particularly preferred.

Preferred tetraalkylpiperidine compounds are those of the formulae II to VI wherein $R_8$ is $R_{8a}$, $R_{8a}$ being selected from the group consisting of hydrogen, $C_{1-4}$alkyl, ($C_{1-4}$alkyl) carbonyl and $C_{1-8}$alkoxy. In a most preferred embodiment, $R_{8a}$ is $R_{8b}$, wherein $R_{8b}$ is selected from hydrogen, methyl, acetyl and octyloxy.

In a further preferred embodiment of the invention, a composition according to the invention also comprises at least one UV-absorbing benzotriazole. Benzotriazoles have been known for some time as UV stabilizers and any such benzotriazoles may be used in this invention. Preferred benzotriazole compounds for use in this invention correspond to the formula VIII

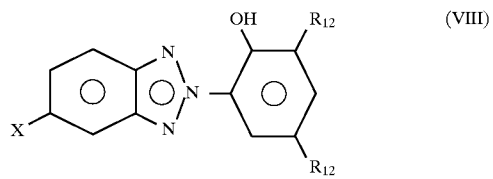

(VIII)

wherein

X is selected from hydrogen, halogen, $C_{1-18}$alkyl and $C_{1-18}$alkoxy;

$R_{12}$ is selected from $C_{1-18}$alkyl and $-C(R_{13})_2Ph$ where $R_{13}$ is $C_{1-4}$alkyl and Ph is a phenyl group.

In preferred cases, X is chlorine and $R_{12}$ is selected from butyl, nonyl and $-C(CH_3)_2Ph$.

The diphenyloxamide, the tetraalkylpiperidine and, if present, the benzotriazole may be mixed to form a single composition which may then be used in a practical application. However, they may also be added separately, and in one specialized case which will be further described herein, individual components of the composition may be used in different parts of a coating film.

The diphenyloxamide and the tetraalkylpiperidine in the composition are preferably present in the proportions of from 1:5 to 5:1. When benzotriazole is present it comprises from 5% to 25%, preferably from 10% to 20% by weight of the total composition.

The compositions of the invention are useful as UV stabilizers in polymers. The polymeric material may be any polymeric material and the composition of the invention may be incorporated therein by conventional means. The invention therefore provides a polymeric material comprising a light-stabilizing quantity of a composition as hereinabove described. The invention further provides a process for enhancing the light stability of a polymeric material, comprising the incorporation therein of a composition as hereinabove described. The compositions of the invention are unaffected by normal polymer processing operations and are readily incorporated into polymer systems to make the whole gamut of polymeric articles.

The compositions according to the invention are particularly useful when used as light-stabilizers in coating compositions which are applied to substrates in order to provide thereon a decorative and/or protective polymeric film. They are particularly useful in automotive coating compositions, either OEM of refinish. The invention therefore provides a coating composition stabilized against light degradation by the incorporation therein of a light-stabilizing quantity of a composition as hereinabove described.

The coating composition may comprise any of the normal film-forming polymeric materials in aqueous or non-aqueous media and in solution, dispersion or powder form, and may include polymeric materials such as acrylics, alkyd resins, polyester resins, polyurethane resins, epoxy resins and urea-, melamine- and phenyl-formaldehyde resins. It has been found that this invention gives particularly good results when the coating composition is a basecoat-clearcoat composition. In such a composition, there is applied to a substrate a coloured basecoat to which is then applied (generally while the basecoat is still wet) a transparent or "clear" topcoat. This gives a finish with a high gloss and "deep" colour appearance and such compositions are currently much used in the automotive field. Such coatings can, however, be particularly susceptible to UV damage. This invention allows the formulation of a basecoat-clearcoat composition which exhibits particularly good UV resistance. The invention therefore also provides a coating film which comprises at least two coats, at least one coloured basecoat and at least one transparent topcoat, a composition according to the present invention being present in at least one basecoat, at least one topcoat or in both at least one basecoat and at least one topcoat. In an especially preferred embodiment, the diphenyloxamide and the tetraalkylpiperidine are present in at least one clear topcoat and benzotriazole is present in at least one coloured basecoat. The invention therefore also provides a coating film which comprises at least two coats, at least one coloured basecoat and at least one transparent topcoat, and a composition as hereinabove described wherein there is included at least one benzotriazole, the benzotriazole being incorporated into at least one basecoat and the other components of the composition being incorporated into at least one topcoat.

The compositions according to the invention may, depending on their compatibility with the particular film-forming system, be added directly to the system or be initially dissolved or dispersed in a suitable solvent prior to addition thereto.

The coating compositions according to this invention exhibit excellent properties. Even after prolong exposure to light, the gloss remains high and there is little cracking. This is especially noticeable when basecoat-clearcoat compositions according to the invention are compared with known compositions of this type.

The quantity of composition needed to confer an appreciable extent of light stabilization on a polymeric composition varies with type and end use of polymer but is generally appreciably lower that the required quantity of conventional light stabilizers. The skilled person can readily ascertain the appropriate quantity for any given case but typical quantities are from 0.01 to 8.0%, more preferably from 0.2 to 4.0% by weight of the polymer.

The invention is further illustrated by means of the following examples in which all parts are expressed by weight.

EXAMPLE 1

Use of a composition according to the invention in a basecoatclearcoat composition. The composition according to the invention comprised a mixture of equal weights of compound Ia and compound II, wherein in compound II $R_5$ is the group $-(CH_2)_2COOC_{12}H_{25}$ $R_7$ is methyl and $R_8$ is hydrogen.

A clear coating composition is prepared by blending 80 parts of a 50% solution of "Viacryl" SC344 (ex Vianova Kunstharz) acrylic resin, 13.9 parts of "Mafrenal" MF80 (ex Hoechst) melamine resin and 4.1 parts of "Byketal" OK (ex Byk-Mallinkrodt) solvent.

The composition of the invention as hereinabove described is dissolved in a solvent compatible with the solvents of the resins and stirred into the resin blend at a rate of 3 parts of composition solids per 100 parts of resin solids.

The coating composition is used as the clear topcoat of a basecoatclearcoat system and it is applied conventionally to a still wet coloured basecoat to give a film thickness of 30–40 μm. The coating composition is cured at 250° C. for 30 minutes and subjected to a standard UV and weathering testing regime. As a control, a coating composition identical to that just described but lacking the composition according to the invention is applied, cured and tested in identical fashion. The coating composition according to the invention exhibits appreciably superior resistance to UV light and weathering.

EXAMPLE 2

A coating composition prepared by blending a polyester resin and a polyisocyanate in the weight ratio of 2:1. To this blend is added a composition according to the invention, this composition being a mixture of compound Ia and compound II as describe in Example 1, the weight proportion of Ia:II being 2:1.

The resulting clear coating composition is used as a topcoat in a basecoat-clearcoat composition and is sprayed out and tested in the same manner as is the coating composition of Example 1. The same excellent results are obtained in comparison to an otherwise identical control which lacked the composition according to the invention.

EXAMPLE 3

The following components were blended to form a homogeneous mixture:
"Setalux" C-1502 XX-60 29.5 parts (ex Synthese B.V.—a 60% solution of an acrylic resin)
"Setalux" C-1382 BX-45 39.2 parts (a 45% solution of an acrylic resin)
"Setamine" US-138 BB-70 21.4 parts (ex Synthese B.V.—a 70% solution of a melamine resin)
"Baysilonoil" 2.5 parts (ex Bayer—a 2% xylene solution of a silicon oil)
"Depanol" Y solvent 7.4 parts (ex Hoechst)
Composition from Example 1 2.5 parts
Phosphoric acid catalyst 2.0 parts
This composition was used as a clearcoat in a basecoat-clearcoat composition. It was sprayed on a still-wet coloured basecoat to give a film of thickness 30–40 μm and baked at 110° C. for 20 minutes. In UV and weathering testing, the coating composition comprising the composition according to the invention significantly outperforms a control which is identical except for the lack of the composition according to the invention.

EXAMPLE 4

A composition according to the invention as described in Example I was added at a rate of 2% by weight to a pigmented finish based on a commercial polyurethane resin. A 20–30 μm film is applied to primed metal panels by spraying, allowed to stand at room temperature for 30 minutes and then baked at 120° C. for 30 minutes. A series of control panels are also prepared, these being identical except for the absence from the pigments finish of the composition according to the invention.

In subsequent UV and weathering testing, the panels coated with the finish containing the composition according to the invention perform significantly better than the control panels.

EXAMPLE 5

An automotive base coat based on a thermosetting acrylic resin and containing 40% resin solids is mixed with 1%, based on the weight of resin solids, of a benzotriazole light stabilizer ("Tinuvin" 328) and 0.8%, based on the weight of resin solids, of p-toluenesulfonic acid.

A solution of 2.79 parts of the compounds of formula Ia dissolved in 75 parts cyclohexanone is mixed with an automotive clear coat based on a thermosetting acrylic resin to which has previously been added the compound of formula II used in Example I and an acid catalyst, such as dodecylbenzene sulfonic acid or p-toluenesulfonic acid. The clear coat contains 62% resin solids and the amounts of the aforementioned components are such that the resulting mixture contains 3% compound of formula Ia, 0.5% compound of formula II and about 0.8% acid catalyst, based on the weight of the resin solids.

The base coat and clear coat prepared as above are each diluted with xylene to a viscosity suitable for spray application and are sprayed on an aluminum panel which has been conversion coated with a chemical composition ("Alodine"). The base coat is applied to a thickness of 0.6 to 0.8 mil, followed by a wet-on-wet application of the clear coat to a thickness of 1.7 to 2.0 mils. The coated panel is then baked at 121° C. for 30 minutes. The resulting coating shows excellent gloss retention and resistance to cracking when exposed to ultraviolet light.

We claim:

1. A non-aqueous coating composition comprising a) a film forming polymeric material b) an effective amount of a light stabilizing composition which consists of
  (1) tetraalkylpiperidine,
  (2) diphenyloxamide and
  (3) a UV absorbing benzotriazole of the formula X

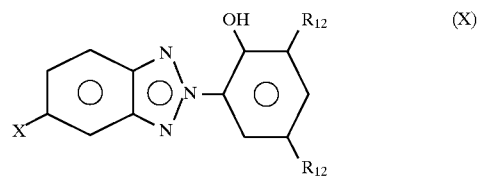

wherein
X is selected from hydrogen, halogen, $C_{1-18}$alkyl and $C_{1-18}$alkoxy;
$R_{12}$ is selected from $C_{1-18}$alkyl and —$C(R_{13})_2$Ph where $R_{13}$ is $C_{1-4}$alkyl and Ph is a phenyl group, wherein said diphenyloxamide is selected from compounds of formula I

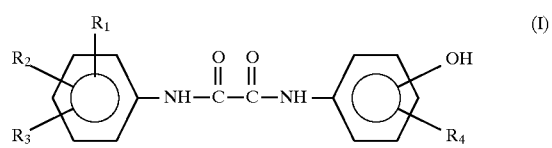

wherein $R_1$ is selected from hydrogen $C_{1-20}$alkyl, $C_{1-20}$alkoxy and halogen;

$R_2$ is selected from hydrogen $C_{1-20}$alkyl, $C_{1-20}$alkoxy, halogen, phenyl and phenoxy; and $R_3$ and $R_4$ are selected form hydrogen, $C_{1-20}$alkyl, $C_{1-20}$alkoxy; and wherein said tetraalkylpiperidine is selected from compounds of formulae II–IX

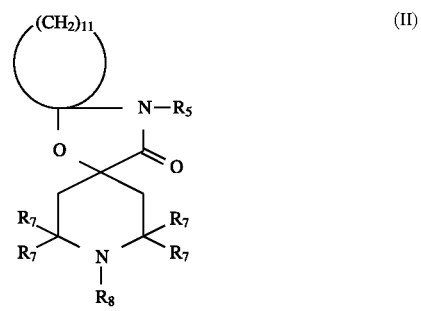

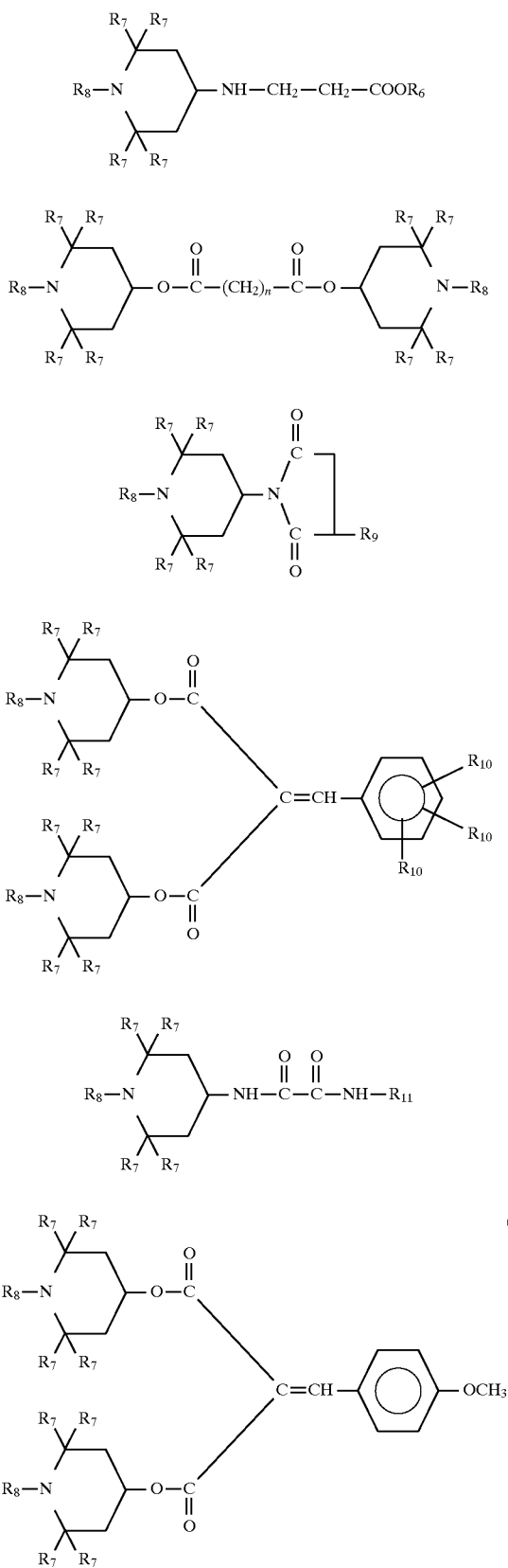

(III)
(IV)
(V)
(VI)
(VII)
(VIII)

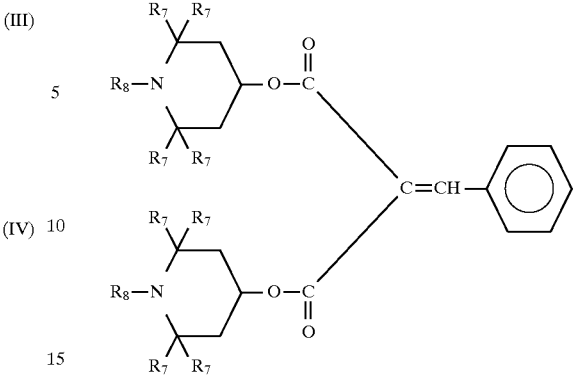

(IX)

wherein $R_5$ is selected from hydrogen and a group of the formula —$(CH_2)_n$—$COOR_6$ wherein $R_6$ is $C_{1-12}$alkyl;

each $R_7$ is selected from $C_{1-6}$alkyl, preferably methyl, or two groups $R_7$ attached to the same piperidine carbon atom form together with that carbon atom a saturated isocyclic ring of six carbon atoms maximum;

$R_8$ is selected from hydrogen, $C_{1-12}$alkyl, $C_{1-12}$alkenylcarbonyl, $C_{1-12}$alkoxy, —$COR_{13}$ where $R_{13}$ is —$C(R_{14})=CH_2$; $C_{1-6}$ alkyl; phenyl; —$NR_{15}R_{16}$; —CO—$C_6H_5$; —$CH_2C_6H_5$; $COOC_{1-12}$alkyl or —COOH; $R_{15}$ is hydrogen, $C_{1-12}$alkyl, $C_{5-6}$cycloalkyl, phenyl, phenyl $C_{1-4}$alkyl or $C_{1-12}$ alkylphenyl and $R_{16}$ is hydrogen or $_{1-12}$alkyl; and $R_{14}$ is hydrogen or $C_{1-6}$alkyl unsubstituted or monosubstituted by OH;

$R_9$ is $C_{1-18}$-alkyl;

$R_{10}$ is independently selected from hydrogen, $C_{1-12}$alkyl, $C_{1-12}$alkoxy, —OH or

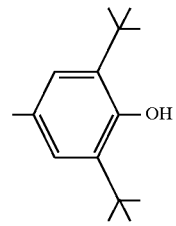

$R_{11}$ is selected from $C_{1-18}$alkoxy and Ph $OCH_2COOR_6$ where Ph is phenyl;

n is a number from 1 to 18; and m is a number from 1 to 4;

the diphenyloxamide and the tetraalkylpiperidine being present in the composition in the proportion of from 1:19 to 19:1.

2. A coating composition according to claim 1 wherein the diphenyloxamine is selected from compounds of the formulae Ia–Ih

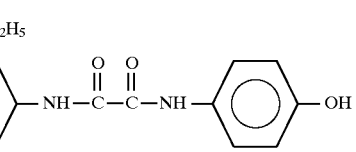

(Ia)

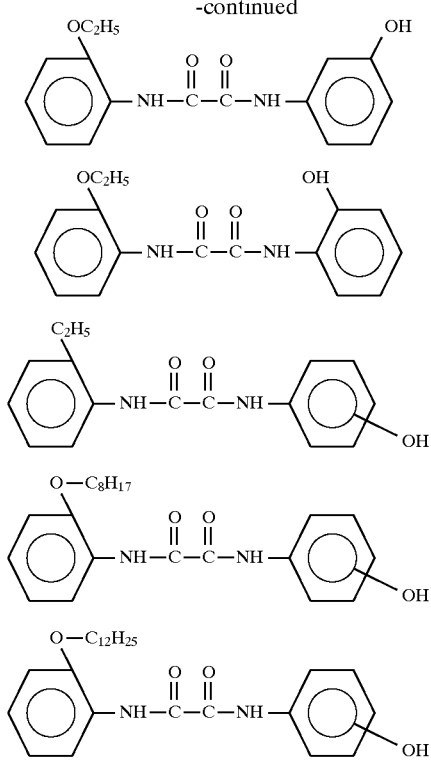
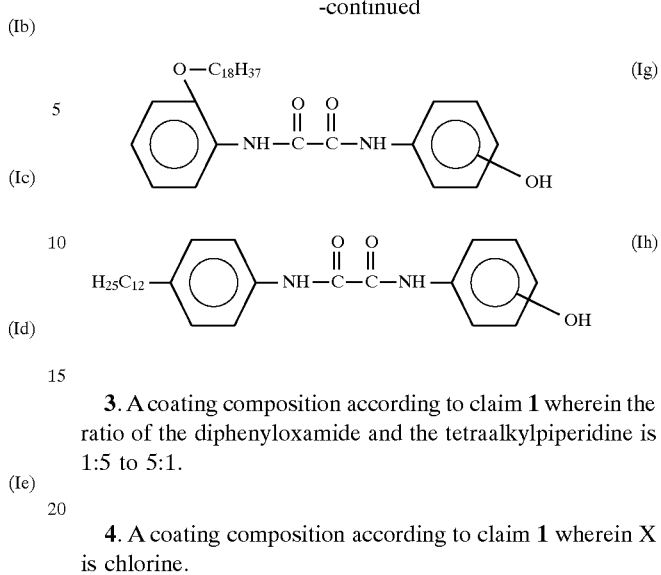
3. A coating composition according to claim 1 wherein the ratio of the diphenyloxamide and the tetraalkylpiperidine is 1:5 to 5:1.
4. A coating composition according to claim 1 wherein X is chlorine.
5. A coating composition according to claim 1 wherein $R_{12}$ is selected from butyl, nonyl and —$(CH_3)_2Ph$.
* * * * *